United States Patent
Dukhovlinov et al.

(10) Patent No.: US 10,662,250 B2
(45) Date of Patent: May 26, 2020

(54) HUMANIZED MONOCLONAL ANTIBODY SPECIFIC TO SYNDECAN-1

(71) Applicants: Ilya Vladimirovich Dukhovlinov, St. Petersburg (RU); Anton Iosifovich Orlov, St. Petersburg (RU); Mark Borisovich Balazovskiy, St. Petersburg (RU)

(72) Inventors: Ilya Vladimirovich Dukhovlinov, St. Petersburg (RU); Anton Iosifovich Orlov, St. Petersburg (RU); Mark Borisovich Balazovskiy, St. Petersburg (RU); Gene Miron Spektor, St. Petersburg (RU)

(*) Notice: Subject to any disclaimer, the term of this patent is extended or adjusted under 35 U.S.C. 154(b) by 46 days.

(21) Appl. No.: 15/745,294

(22) PCT Filed: Jul. 21, 2016

(86) PCT No.: PCT/RU2016/000467
§ 371 (c)(1),
(2) Date: Jan. 16, 2018

(87) PCT Pub. No.: WO2017/014679
PCT Pub. Date: Jan. 26, 2017

(65) Prior Publication Data
US 2019/0002580 A1  Jan. 3, 2019

(30) Foreign Application Priority Data
Jul. 20, 2015 (RU) .................. 2015129656

(51) Int. Cl.
| | | |
|---|---|---|
| *C07K 16/00* | (2006.01) | |
| *C07K 16/28* | (2006.01) | |
| *C07K 16/30* | (2006.01) | |
| *A61P 35/00* | (2006.01) | |
| *A61K 39/00* | (2006.01) | |

(52) U.S. Cl.
CPC .......... *C07K 16/2896* (2013.01); *A61P 35/00* (2018.01); *C07K 16/30* (2013.01); *A61K 2039/505* (2013.01); *C07K 2317/14* (2013.01); *C07K 2317/24* (2013.01); *C07K 2317/526* (2013.01); *C07K 2317/72* (2013.01); *C07K 2317/92* (2013.01)

(58) Field of Classification Search
None
See application file for complete search history.

(56) References Cited

U.S. PATENT DOCUMENTS 5,530,101 A * 6/1996 Queen .................. C07K 16/00
424/133.1
2007/0183971 A1 8/2007 Goldmakher

FOREIGN PATENT DOCUMENTS

| RU | 2486203 | 6/2013 |
|---|---|---|
| WO | 2009080829 | 7/2009 |
| WO | WO2009080829 | * 7/2009 |

OTHER PUBLICATIONS

Tassone P. et al. Cytotoxic activity of the maytansinoid immunoconjugate B-B4-1-3 DMI against CD138+ multiple myeloma cells. Blood, 2004, pp. 3688-3696, vol. 104, No. 12.
International Search Report PCT/RU2016/000467 completed Jan. 13, 2017; dated Feb. 9, 2017 3 pages.
Written Opinion of the International Searching Authority PCT/RU2016/000467 dated Feb. 9, 2017 4 pages.

* cited by examiner

*Primary Examiner* — Meera Natarajan
(74) *Attorney, Agent, or Firm* — The Roy Gross Law Firm, LLC; Roy Gross

(57) ABSTRACT

The present invention relates to immunology, biotechnology and medicine, notably to the field of antitumor pharmaceuticals based on monoclonal antibodies, and can be used in medicine for the treatment of oncological diseases.
The object of the invention was to create an efficient and safe universal antitumor agent, the production of which effective, quick and easy. This problem is solved by the proposed humanized monoclonal antibody specific to syndecan-1, of the IgG4 isotype, or with IgG3 fragments and amino acid substitutions for the increase the antibody half-life, characterized by a definite combination of the calculated and created by the authors amino acid and nucleotide sequences, which is used as a self-acting substance for the therapy of tumor diseases. Nucleotide sequences additionally contain a fragment coding for a signal secretory sequence at the N-terminus, and are codon-optimized to increase antibody production in mammalian cells.

9 Claims, 5 Drawing Sheets

Specification includes a Sequence Listing.

SEQUENCE LISTING

```
<160> NUMBER OF SEQ ID NOS: 12

<210> SEQ ID NO 1
<211> LENGTH: 449
<212> TYPE: PRT
<213> ORGANISM: Artificial sequence
<220> FEATURE:
<223> OTHER INFORMATION: Heavy chain of chimeric IgG4 Mab to CD138
      derived from hybridoma 2

<400> SEQUENCE: 1

Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
                20                  25                  30

Trp Ile Glu Trp Val Lys Gln Arg Pro Gly His Gly Leu Glu Trp Ile
            35                  40                  45

Gly Glu Ile Leu Pro Gly Thr Gly Arg Thr Ile Tyr Asn Glu Lys Phe
        50                  55                  60

Lys Gly Lys Ala Thr Phe Thr Ala Asp Ile Ser Ser Asn Thr Val Gln
65                  70                  75                  80

Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
                100                 105                 110

Gly Gln Gly Thr Ser Val Thr Val Ser Ser Ala Ser Thr Lys Gly Pro
            115                 120                 125
```

```
Ser Val Phe Pro Leu Ala Pro Cys Ser Arg Ser Thr Ser Glu Ser Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Phe Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 2
<211> LENGTH: 1431
<212> TYPE: DNA
<213> ORGANISM: Artificial sequence
<220> FEATURE:
<223> OTHER INFORMATION: nucleotide sequence coding for SEQ ID NO: 1

<400> SEQUENCE: 2
atgggcgtgc acgagtgccc cgcctggctg tggctgctcc tcagtctgct gagcctgccc      60
ctgggcctgc ccgtgctggg ccaggtgcag ctgcagcaga gcggcagcga gctgatgatg     120
cccggcgcca gcgtgaagat cagctgcaag gccaccggct acaccttcag caactactgg     180
atcgagtggg tgaagcagcg ccccggccac ggcctggagt ggatcggcga gatcctgccc     240
```

```
ggcaccggcc gcaccatcta caacgagaag ttcaagggca aggccacctt caccgccgac    300
atcagcagca acaccgtgca gatgcagctg agcagcctga ccagcgagga cagcgccgtg    360
tactactgcg cccgccgcga ctactacggc aacttctact acgccatgga ctactggggc    420
cagggcacca gcgtgaccgt gagcagcgcc agcaccaagg cccccagcgt gttccccctg    480
gccccctgca gccgcagcac cagcgagagc accgccgccc tgggctgcct ggtgaaggac    540
tacttccccg agcccgtgac cgtgagctgg aacagcggcg ccctgaccag cggcgtgcac    600
accttccccg ccgtgctgca gagcagcggc ctgtacagcc tgagcagcgt ggtgaccgtg    660
cccagcagca gcctgggcac caagacctac acctgcaacg tggaccacaa gcccagcaac    720
accaaggtgg acaagcgcgt ggagagcaag tacggccccc cctgccccag ctgccccgcc    780
cccgagttcc tgggcggccc cagcgtgttc ctgttccccc caagcccaa ggacaccctg    840 atgatcagcc gcaccctga agtgacctgc gtggtggtgg acgtgagcca ggaggacccc    900
gaggtgcagt tcaactggta cgtggacggc gtggaggtgc acaacgccaa gaccaagccc    960
cgcgaggagc agttcaacag cacctaccgc gtggtgagcg tgctgaccgt gctgcaccag    1020
gactggctga acggcaagga gtacaagtgc aaggtgagca caagggcct gcccagcagc    1080 atcgagaaga ccatcagcaa ggccaagggc cagccccgcg agccccaggt gtacaccctg    1140 cccccagcc aggaggagat gaccaagaac caggtgagcc tgacctgcct ggtgaagggc    1200
ttctacccca gcgacatcgc cgtggagtgg gagagcaacg gccagcccga gaacaactac    1260
aagaccaccc cccccgtgct ggacagcgac ggcagcttct cctgtacag ccgcctgacc    1320 gtggacaaga gccgctggca ggagggcaac gtgttcagct gcagcgtgat gcacgaggcc    1380
ctgcacaacc actacaccca gaagagcctc agtctgagcc tgggcaagta a            1431
```

<210> SEQ ID NO 3
<211> LENGTH: 214
<212> TYPE: PRT
<213> ORGANISM: Artificial sequence
<220> FEATURE:
<223> OTHER INFORMATION: light chain of chimeric Mab to CD138 derived
      from hybridoma 1

<400> SEQUENCE: 3

```
Asp Ile Gln Met Thr Gln Ser Thr Ser Ser Leu Ser Ala Ser Leu Gly
1               5                   10                  15

Asp Arg Val Thr Ile Ser Cys Ser Ala Ser Gln Gly Ile Asn Asn Tyr
            20                  25                  30

Leu Asn Trp Tyr Gln Gln Lys Pro Asp Gly Thr Val Glu Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Tyr Ser Leu Thr Ile Ser Asn Leu Glu Pro
65                  70                  75                  80

Glu Asp Ile Gly Thr Tyr Tyr Cys Gln Gln Tyr Ser Lys Leu Pro Arg
                85                  90                  95

Thr Phe Gly Gly Gly Thr Lys Leu Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140
```

```
Lys Val Gln Trp Lys Val Asp Asn Ala Leu Gln Ser Gly Asn Ser Gln
145                 150                 155                 160

Glu Ser Val Thr Glu Gln Asp Ser Lys Asp Thr Tyr Ser Leu Ser
            165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 4
<211> LENGTH: 726
<212> TYPE: DNA
<213> ORGANISM: Artificial sequence
<220> FEATURE:
<223> OTHER INFORMATION: nucleotide sequence coding for SEQ ID NO: 3

<400> SEQUENCE: 4

```
atgggcgtgc acgagtgccc cgcctggctg tggctgctcc tcagtctgct gagcctgccc      60
ctgggcctgc ccgtgctggg cgacatccag atgacccaga gcaccagcag cctgagcgca     120
agtctgggcg accgcgtgac catcagctgc agcgccagcc agggcatcaa caactacctg     180
aactggtacc agcagaagcc cgacggcacc gtggagctgc tgatctacta caccagcacc     240
ctgcagagcg gcgtgcccag ccgcttcagt ggcagtggaa gcggcaccga ctacagcctg     300
accatcagca acctggagcc cgaggacatc ggcacctact actgccagca gtacagcaag     360
ctgccccgca ccttcggcgg cggcaccaag ctggagatca gcgcaccgt ggccgccccc      420 agcgtgttca tcttcccccc cagcgacgag cagctgaaga gcggcaccgc cagcgtggtg     480
tgcctgctga acaacttcta ccccgcgag gccaaggtgc agtggaaggt ggacaacgcc      540
ctgcagagcg gcaacagcca ggagagcgtg accgagcagg acagcaagga cagcacctac     600
agcctcagta gcaccctgac cctgagcaag gccgactacg agaagcacaa ggtgtacgcc     660
tgcgaggtga cccaccaggg cctgagcagc cccgtgacca gagcttcaa ccgcggcgag      720 tgctaa                                                                726
```

<210> SEQ ID NO 5
<211> LENGTH: 449
<212> TYPE: PRT
<213> ORGANISM: Artificial sequence
<220> FEATURE:
<223> OTHER INFORMATION: heavy chain of humanized IgG4 Mab to CD138
      derived from hybridoma 1

<400> SEQUENCE: 5

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Trp Met His Trp Val Arg Gln Ala Pro Gly Gln Gly Leu Glu Trp Met
        35                  40                  45

Gly Ile Ile Leu Pro Gly Thr Gly Arg Thr Ser Tyr Ala Gln Lys Phe
    50                  55                  60

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
                85                  90                  95
```

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
                180                 185                 190

Val Pro Ser Ser Ser Leu Gly Thr Lys Thr Tyr Thr Cys Asn Val Asp
                195                 200                 205

His Lys Pro Ser Asn Thr Lys Val Asp Lys Arg Val Glu Ser Lys Tyr
            210                 215                 220

Gly Pro Pro Cys Pro Ser Cys Pro Ala Pro Glu Phe Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
                260                 265                 270

Pro Glu Val Gln Phe Asn Trp Tyr Val Asp Gly Val Glu Val His Asn
            275                 280                 285

Ala Lys Thr Lys Pro Arg Glu Glu Gln Phe Asn Ser Thr Tyr Arg Val
            290                 295                 300

Val Ser Val Leu Thr Val Leu His Gln Asp Trp Leu Asn Gly Lys Glu
305                 310                 315                 320

Tyr Lys Cys Lys Val Ser Asn Lys Gly Leu Pro Ser Ser Ile Glu Lys
                325                 330                 335

Thr Ile Ser Lys Ala Lys Gly Gln Pro Arg Glu Pro Gln Val Tyr Thr
                340                 345                 350

Leu Pro Pro Ser Gln Glu Glu Met Thr Lys Asn Gln Val Ser Leu Thr
            355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
            435                 440                 445

Lys

<210> SEQ ID NO 6
<211> LENGTH: 1431
<212> TYPE: DNA
<213> ORGANISM: Artificial sequence
<220> FEATURE:
<223> OTHER INFORMATION: nucleotide sequence coding for SEQ ID NO: 5

<400> SEQUENCE: 6

```
atgggcgtgc acgagtgccc cgcctggctg tggctgctcc tcagtctgct gagcctgccc    60
ctgggcctgc ccgtgctggg ccaggtgcag ctggtgcaga gcggcgccga ggtgaagaag   120
cccggcgcca gcgtgaaggt gagctgcaag gccagcggct acaccttcag caactactgg   180
atgcactggg tgcgccaggc ccccggccag ggcctggagt ggatgggcat catcctgccc   240
ggcaccggcc gcaccagcta cgcccagaag ttccagggcc gcgtgaccat gacccgcgac   300
acaagtacta gcaccgtgta catggagctg agcagcctgc gcagcgagga caccgccgtg   360
tactactgcg cccgccgcga ctactacggc aacttctact acgccatgga ctactgggga   420
caaggcacca gcgtgaccgt gagcagcgcc agcaccaagg gccccagcgt gttccccctg   480
gcccctgca gccgcagcac cagcgagagc accgccgccc tgggctgcct ggtgaaggac   540
tacttccccg agcccgtgac cgtgagctgg aacagcggcg ccctgaccag cggcgtgcac   600
accttccccg ccgtgctgca gagcagcggc ctgtacagcc tgagcagcgt ggtgaccgtg   660
cccagcagca gcctgggcac caagacctac acctgcaacg tggaccacaa gcccagcaac   720
accaaggtgg acaagcgcgt ggagagcaag tacggccccc cctgccccag ctgccccgcc   780
cccgagttcc tgggcggccc cagcgtgttc ctgttccccc caagcccaa ggacaccctg   840
atgatcagcc gcacccctga agtgacctgc gtggtggtgg acgtgagcca ggaggacccc   900
gaggtgcaat taactggta cgtggacggc gtggaggtgc acaacgccaa gaccaaacca   960
cgtgaggagc agttcaacag cacctaccgc gtggtgagcg tgctgaccgt gctgcaccag  1020
gactggctga acggcaagga gtacaagtgc aaggtgagca acaagggcct gccagcagc  1080
atcgagaaga ccatcagcaa ggccaagggc cagccccgcg agcccagt gtacaccctg  1140
cccccagcc aggaggagat gaccaagaac caggtgagcc tgacctgcct ggtgaagggc  1200
ttctacccca gcgacatcgc cgtggagtgg gagagcaacg gccagcccga gaacaactac  1260
aagaccaccc cccccgtgct ggacagcgac ggcagcttct tcctgtacag ccgcctgacc  1320
gtggacaaga gccgctggca ggagggcaac gtgttcagct gcagcgtgat gcacgaggcc  1380
ctgcacaacc actacaccca gaagagcctt agtctgagcc tgggcaagta a           1431
```

<210> SEQ ID NO 7
<211> LENGTH: 214
<212> TYPE: PRT
<213> ORGANISM: Artificial sequence
<220> FEATURE:
<223> OTHER INFORMATION: light chain of humanized Mab to CD138 derived
      from hybridoma 2

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Asn Asn Tyr
            20                  25                  30

Leu Ala Trp Tyr Gln Gln Lys Pro Gly Lys Val Pro Lys Leu Leu Ile
        35                  40                  45

Tyr Tyr Thr Ser Thr Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Val Ala Thr Tyr Tyr Cys Gln Gln Tyr Ser Lys Leu Pro Arg
                85                  90                  95

Thr Phe Gly Gly Gly Thr Lys Leu Glu Ile Lys Arg Thr Val Ala Ala
            100                 105                 110
```

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
            165                 170                 175

Ser Thr Leu Thr Leu Ser Lys Ala Asp Tyr Glu Lys His Lys Val Tyr
        180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 8
<211> LENGTH: 726
<212> TYPE: DNA
<213> ORGANISM: Artificial sequence
<220> FEATURE: nucleotide sequence coding for SEQ ID NO: 7

<400> SEQUENCE: 8

```
atgggcgtgc acgagtgccc cgcctggctg tggctgctcc tcagtctgct gagcctgccc      60
ctgggcctgc ccgtgctggg cgacatccag atgacccaga gcccagtag tctgagcgct     120
agtgtcggcg accgcgtgac catcacctgc cgcgccagcc agggcatcaa caactacctg     180
gcctggtacc agcagaagcc cggcaaggtg cccaagctgc tgatctacta caccagcacc     240
ctgcagagcg gcgtgcccag ccgcttcagt ggaagcggaa gcggtactga cttcaccctg     300
accatcagca gcctgcagcc cgaggacgtg gccacctact actgccagca gtacagcaag     360
ctgccccgca ccttcggcgg cggcaccaag ctggagatca gcgcaccgt ggccgccccc      420
agcgtgttca tcttcccccc cagcgacgag cagctgaaga gcggcaccgc cagcgtggtg     480
tgcctgctga caacttccta ccccgcgag gccaaggtgc agtggaaggt ggacaacgcc      540
ctgcagagcg gcaacagcca ggagagcgtg accgagcagg acagcaagga cagcacctac     600
agcctcagta gcaccctgac cctgagcaag gccgactacg agaagcacaa ggtgtacgcc     660
tgcgaggtga cccaccaggg cctgagcagc ccgtgacca gagcttcaa ccgcggcgag       720
tgctaa                                                                726
```

<210> SEQ ID NO 9
<211> LENGTH: 449
<212> TYPE: PRT
<213> ORGANISM: Artificial sequence
<220> FEATURE:
<223> OTHER INFORMATION: heavy chain of humanized IgG4-IgG3 Mab to CD138
      derived from hybridoma 1

<400> SEQUENCE: 9

```
Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asn Tyr
            20                  25                  30

Trp Met His Trp Val Arg Gln Ala Pro Gly Gln Gly Leu Glu Trp Met
        35                  40                  45

Gly Ile Ile Leu Pro Gly Thr Gly Arg Thr Ser Tyr Ala Gln Lys Phe
    50                  55                  60
```

Gln Gly Arg Val Thr Met Thr Arg Asp Thr Ser Thr Ser Thr Val Tyr
65                  70                  75                  80

Met Glu Leu Ser Ser Leu Arg Ser Glu Asp Thr Ala Val Tyr Tyr Cys
            85                  90                  95

Ala Arg Arg Asp Tyr Tyr Gly Asn Phe Tyr Tyr Ala Met Asp Tyr Trp
        100                 105                 110

Gly Gln Gly Thr Ser Val Thr Val Ser Ser Ala Ser Thr Lys Gly Pro
    115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
    210                 215                 220

Gly Pro Pro Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 10
<211> LENGTH: 1431
<212> TYPE: DNA

<213> ORGANISM: Artificial sequence
<220> FEATURE:
<223> OTHER INFORMATION: nucleotide sequence coding for SEQ ID NO: 9

<400> SEQUENCE: 10

```
atgggcgtgc acgagtgccc cgcctggctg tggctgctcc tcagtctgct gagcctgccc      60
ctgggcctgc ccgtgctggg ccaggtgcag ctggtgcaga gcggcgccga ggtgaagaag     120
cccggcgcca gcgtgaaggt gagctgcaag gccagcggct acaccttcag caactactgg     180
atgcactggg tgcgccaggc ccccggccag ggcctggagt ggatgggcat catcctgccc     240
ggcaccggcc gcaccagcta cgcccagaag ttccagggcc gcgtgaccat gacccgcgac     300
acaagtacta gcaccgtgta catggagctg agcagcctgc gcagcgagga caccgccgtg     360
tactactgcg cccgccgcga ctactacggc aacttctact acgccatgga ctactgggga     420
caaggcacca gcgtgaccgt gagcagcgcc agcaccaagg gccccagcgt gttccccctg     480
gcccccctgca gccgcagcac cagcgagagc accgccgccc tgggctgcct ggtgaaggac     540
tacttccccg agcccgtgac cgtgagctgg aacagcggcg ccctgaccag cggcgtgcac     600
accttccccg ccgtgctgca gagcagcggc ctgtacagcc tgagcagcgt ggtgaccgtg     660
cccagcagca gcctgggcac caagacctac acctgcaacg tggaccacaa gcccagcaac     720
accaaggtgg acaagcgcgt ggagagcaag tacggccccc cctgccccag ctgccccgcc     780
cccgagctgc tgggcggccc cagcgtgttc ctgttccccc caagcccaa ggacaccctg      840
atgatcagcc gcaccctga agtgacctgc gtggtggtgg acgtgagcca ggaggacccc     900
gaggtgcagt tcaactggta cgtggacggc gtggaggtgc acaacgccaa gaccaagccc     960
cgcgaggagc agtacaacag cacctaccgc gtggtgagcg tgctgaccgt gctgcaccag    1020
gactggctga acggcaagga gtacaagtgc aaggtgagca caaggccct gcccgcacct    1080
atcgagaaga ccatcagcaa ggccaagggc cagccccgcg agccccaggt gtacaccctg    1140
cccccagcc aggaggagat gaccaagaac caggtgagcc tgacctgcct ggtgaagggc    1200
ttctacccca gcgacatcgc cgtggagtgg gagagcaacg ccagcccga aacaactac      1260
aagaccaccc cccccgtgct ggacagcgac ggcagcttct cctgtacag ccgcctgacc     1320
gtggacaaga gccgctggca ggagggcaac gtgttcagct gcagcgtgat gcacgaggcc    1380
ctgcacaacc actacaccca gaagagcctc agtctgagcc tgggcaagta a             1431
```

<210> SEQ ID NO 11
<211> LENGTH: 449
<212> TYPE: PRT
<213> ORGANISM: Artificial sequence
<220> FEATURE:
<223> OTHER INFORMATION: heavy chain of chimeric IgG4-IgG3 Mab to CD138
      derived from hybridoma 2

<400> SEQUENCE: 11

```
Gln Val Gln Leu Gln Gln Ser Gly Ser Glu Leu Met Met Pro Gly Ala
1               5                   10                  15

Ser Val Lys Ile Ser Cys Lys Ala Thr Gly Tyr Thr Phe Ser Asn Tyr
            20                  25                  30

Trp Ile Glu Trp Val Lys Gln Arg Pro Gly His Gly Leu Glu Trp Ile
        35                  40                  45

Gly Glu Ile Leu Pro Gly Thr Gly Arg Thr Ile Tyr Asn Glu Lys Phe
    50                  55                  60

Lys Gly Lys Ala Thr Phe Thr Ala Asp Ile Ser Ser Asn Thr Val Gln
65                  70                  75                  80
```

```
Met Gln Leu Ser Ser Leu Thr Ser Glu Asp Ser Ala Val Tyr Tyr Cys
                85                  90                  95

Ala Arg Arg Asp Tyr Tyr Gly Asn Phe Tyr Tyr Ala Met Asp Tyr Trp
            100                 105                 110

Gly Gln Gly Thr Ser Val Thr Val Ser Ser Ala Ser Thr Lys Gly Pro
        115                 120                 125

Ser Val Phe Pro Leu Ala Pro Cys Ser Arg Ser Thr Ser Glu Ser Thr
130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Lys Thr Tyr Thr Cys Asn Val Asp
        195                 200                 205

His Lys Pro Ser Asn Thr Lys Val Asp Lys Arg Val Glu Ser Lys Tyr
210                 215                 220

Gly Pro Pro Cys Pro Ser Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser Gln Glu Asp
            260                 265                 270

Pro Glu Val Gln Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Gln Glu Glu Met Thr Lys Asn Gln Val Ser Leu Thr
        355                 360                 365

Cys Leu Val Lys Gly Phe Tyr Pro Ser Asp Ile Ala Val Glu Trp Glu
370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Arg Leu Thr Val Asp Lys
                405                 410                 415

Ser Arg Trp Gln Glu Gly Asn Val Phe Ser Cys Ser Val Met His Glu
            420                 425                 430

Ala Leu His Asn His Tyr Thr Gln Lys Ser Leu Ser Leu Ser Leu Gly
        435                 440                 445

Lys

<210> SEQ ID NO 12
<211> LENGTH: 1431
<212> TYPE: DNA
<213> ORGANISM: Artificial sequence
<220> FEATURE:
<223> OTHER INFORMATION: nucleotide sequence coding for SEQ ID NO: 11
```

```
<400> SEQUENCE: 12
atgggcgtgc acgagtgccc cgcctggctg tggctgctcc tcagtctgct gagcctgccc      60
ctgggcctgc ccgtgctggg ccaggtgcag ctgcagcaga gcggcagcga gctgatgatg     120
cccggcgcca gcgtgaagat cagctgcaag gccaccggct acaccttcag caactactgg     180
atcgagtggg tgaagcagcg cccccggccac ggcctggagt ggatcggcga gatcctgccc    240
ggcaccggcc gcaccatcta caacgagaag ttcaagggca aggccacctt caccgccgac     300
atcagcagca acaccgtgca gatgcagctg agcagcctga ccagcgagga cagcgccgtg     360
tactactgcg cccgccgcga ctactacggc aacttctact acgccatgga ctactggggc     420
cagggcacca gcgtgaccgt gagcagcgcc agcaccaagg gcccagcgt gttccccctg      480
gcccctgca gccgcagcac cagcgagagc accgccgccc tgggctgcct ggtgaaggac     540
tacttccccg agcccgtgac cgtgagctgg aacagcggcg ccctgaccag cggcgtgcac     600
accttccccg ccgtgctgca gagcagcggc ctgtacagcc tgagcagcgt ggtgaccgtg    660
cccagcagca gcctgggcac caagacctac acctgcaacg tggaccacaa gcccagcaac    720
accaaggtgg acaagcgcgt ggagagcaag tacggcccc cctgccccag ctgccccgcc    780
cccgagctgc tgggcggccc cagcgtgttc ctgttccccc ccaagcccaa ggacaccctg   840
atgatcagcc gcaccctga agtgacctgc gtggtggtgg acgtgagcca ggaggacccc    900
gaggtgcagt tcaactggta cgtggacggc gtggaggtgc acaacgccaa gaccaagccc   960
cgcgaggagc agtacaacag cacctaccgc gtggtgagcg tgctgaccgt gctgcaccag  1020
gactggctga acggcaagga gtacaagtgc aaggtgagca caaggccct gcccgcacct  1080
atcgagaaga ccatcagcaa ggccaagggc cagccccgcg agccccaggt gtacaccctg  1140
ccccccagcc aggaggagat gaccaagaac caggtgagcc tgacctgcct ggtgaagggc  1200
ttctacccca gcgacatcgc cgtggagtgg gagagcaacg gccagcccga gaacaactac  1260
aagaccaccc ccccccgtgct ggacagcgac ggcagcttct tcctgtacag ccgcctgacc  1320
gtggacaaga gccgctggca ggagggcaac gtgttcagct gcagcgtgat gcacgaggcc  1380
ctgcacaacc actacaccca gaagagcctc agtctgagcc tgggcaagta a            1431
```

HUMANIZED MONOCLONAL ANTIBODY SPECIFIC TO SYNDECAN-1

CROSS-REFERENCE TO RELATED APPLICATIONS

This application is a National Phase of PCT Patent Application No. PCT/RU2016/000467 having International filing date of Jul. 21, 2016, which claims the benefit of priority of Russian Application No. 2015129656 filed on Jul. 20, 2015 entitled HUMANIZED MONOCLONAL ANTIBODY SPECIFIC TO SYNDECAN-1. The contents of the above applications are all incorporated by reference as if fully set forth herein in their entirety.

REFERENCE TO AN ELECTRONIC SEQUENCE LISTING

The contents of the electronic sequence listing (07216-P0002A-Sequence-Listing-Dukhovlinov-revised-v3; Size: 28 kilobytes; and Date of Creation: Apr. 6, 2018) is herein incorporated by reference in its entirety.

FIELD OF THE INVENTION

An embodiment of a present invention relates to immunology, biotechnology and medicine, notably to the field of antitumor pharmaceuticals based on monoclonal antibodies, and can be used in medicine for the treatment of oncological diseases.

BACKGROUND OF THE INVENTION

Oncological diseases are the second most common cause of death after cardiovascular diseases [http://www.who.int/healthinfo/EN_WHS2012_Full.pdf]. According to different sources, in the last 10 years the number of people diagnosed with cancer increased by 15%. In Russian Federation, more than 490 thousand new patients are registered annually, 2.5 million cancer carriers are under the care of a doctor, and more than 290 thousand of cancer-stricken die from different cancer forms every year. For this reason, the development and creation of safe, effective and affordable antitumor pharmaceuticals is essential.

One type of antitumor pharmaceuticals refers to products of biotechnological synthesis—monoclonal antibodies (MAbs). Several pharmaceuticals are currently in use, among them there are MAbs to epidermal growth factor receptor, to vascular endothelial growth factor, which are proven to have an effect on tumor cells activity and possess an insufficient influence on the functioning of normal cells of different tissues [Zhukov N. V., Tjulandin S. A. Targeted therapy in the treatment of solid tumors: practice contradicts theory/Biochemistry (Mosc). 2008 May; 73(5):605-18].

In the world approximately 10 antitumor pharmaceuticals based on monoclonal antibodies are registered and produced currently, notably rituximab (MAb to CD20 receptor), trastuzumab (HER2neu receptor is the target), bevacizumab (VEGF), cetuximab and panitumumab (EGFR). At present, no registered pharmaceuticals exist which target a surface antigen syndecan-1 (CD138).

Syndecan-1 protein (CD138) [Wijdenes J., Dore J. M., Clement C., Vermot-Desroches C. (2003). "CD138". J. Biol. Regul. Homeost. Agents 16 (2): 152-5] is a promising target for antitumor therapy with monoclonal antibodies: it is proven that this molecule plays an important role in the tumor cells activity and it is revealed that it possesses an insufficient influence on the functioning of the normal cells of various tissues [Guo P. et al. Expression of legumain correlates with prognosis and metastasis in gastric carcinoma//PloS One. 2013. Vol. 8, No 9. P. e73090].

This molecule provides cell-cell and cell-matrix interactions, adhesion and migration. Overexpression of CD138 was revealed in the majority (approximately 90%) of cells of various tumor types, including breast, colon, gastric, prostate cancer and of other epithelial malignancies [Rousseau et al. EJNMMI Research 2011, Bayer-Garner I. B., Sanderson R. D., Dhodapkar M. V. et al. Syndecan-1 (CD138) immunoreactivity in bone marrow biopsies of multiple myeloma: shed syndecan-1 accumulates in fibrotic regions. Mod Pathol 2001; 14:1052-8]. Such phenomenon as a loss of syndecan-1 from the cell surface of myeloid cells and its accumulation in stroma, as a rule, in fibrotic regions, is also described [Baikov V. V. Difficulties in morphological diagnostics of multiple myeloma. Moscow, Oncohematology 2'2007, p.p. 10-15]. It is revealed that under the loss of syndecan-1 myeloid cells undergo TRAIL-induced apoptosis [Wu Y. H., Yang C. Y., Chien W. L., Lin K. I., Lai M. Z. Removal of syndecan-1 promotes TRAIL-induced apoptosis in myeloma cells. J Immunol. 2012 Mar 15; 188(6):2914-21. Epub 2012 Feb 3]. Syndecan-1 is connected functionally with the invasive growth and metastatic propensity of the tumor cells. In terms of the malignancies therapy the activity of CD138 is associated with such properties of tumor cells, which almost do not respond to existing therapies.

The localization of CD138 on the surface of the tumor cells in the form, which can be recognized by antibodies, is revealed [Wu B. et al. Blastocystis legumain is localized on the cell surface, and specific inhibition of its activity implicates a pro-survival role for the enzyme//J. Biol. Chem. 2010. Vol. 285, No 3. P. 1790-1798]. Moreover, the data exist, which reveal the effectiveness of vaccination using CD138 as an antigen [Bae J., Tai Y. T., Anderson K. C., Munshi N. C. 2011].

The murine antibodies to syndecan-1 are currently in use—B-B4 (IgG1) [Wijdenes J., Vooijs W. C., Clement C. et al. A plasmacyte selective monoclonal antibody (B-B4) recognizes syndecan-1. Br. J. Haematol 1996; 94:318-23], B-B2 (IgG2b), as well as chimeric antibodies [Baikov V. V. 2007, Kovrigina A. M., Probatova N. A. Differential diagnostics of non-Hodgkin's B-cell's lymphoma. Oncohematology. 2'2007, p.6]—MI15 (IgG1κ)—and their conjugates with tags [ClinicalTrials.gov identifier: NCT01296204, Gattei V., Godeas C., Degan M., Rossi F. M., Aldinucci D., Pinto A. Characterization of anti-CD138 monoclonal antibodies as tools for investigating the molecular polymorphism of syndecan-1 in human lymphoma cells. Br J Haematol. 1999 January; 104(1):152-62]. Such compounds are used for the purpose of research or diagnostics, the antibody performing only the targeting function [Baikov V. V. 2007, Kovrigina A. M., Probatova N. A., 2007]. The cytotoxic functions are performed by the effector molecules, which are mostly conjugated with the antibody [WO2009080832 (A1), WO2009080830 (A1), WO2010128087 (A2)]. Murine and rabbit MAbs are recognized by human immune system as foreign because of differences in the constant domains of the antibodies ($C_H$, $C_L$), and an immune response against them is elicited. For the purpose of use in humans, chimeric antibodies are being developed, which possess human constant domains ($C_H$, $C_L$) and murine variable domains ($V_H$, $V_L$). This modification allows making the MAbs safer. Chimeric monoclonal antibody to CD138 of subclass IgG4 is known [WO2009080829 (A1)], which is considered the prototype by the authors of the present invention. However, this MAb provides only targeting of a cytotoxic agent conjugated thereto (DM4).

A number of inventions is known, where antibodies to CD138 are mentioned, but the structure of these antibodies is not given. Antibody to human CD138 is known having a modification of glycosylation, obtained with the use of a cell expressing at least one nucleic acid encoding (1,4)-N-acetyl-glucosaminiltransferase III (GnT III), and at least one transfected nucleic acid encoding human anti-CD138 antibody, but the amino acid and/or nucleotide sequences of such antibody are not given, the structure of such antibody is not characterized [RU2321630C2]. A variant of invention is known, wherein the anti-CD138 antibody is co-administered with a conjugate of anti-Trop-2 antibody and a chemotherapeutic agent or a conjugate of antibody to mucin or its antigen-binding fragment and a radionuclide for the treatment of pancreatic cancer [US2014044640 (A1)]. Conjugate is known of antibody, which binds to CD138, and of anti-CD74 antibody [US2014056917A1], and of SN38 molecule [US2014058067 (A1)], including fragments thereof, as part of an antibody bispecific structure [US2014086832 (A1)]. Composition is also known containing an anchor region capable of binding to a plasma cell and a site binding to specific plasma cell antibodies which is bound to the anchor region, an antibody capable of binding to syndecan-1 may be a part of the design [WO2014037519 (A2)].

A recombinant antibody to syndecan-1 is currently in use (OC-46F2), produced as a result of in vitro phage-display library selection (ETH-2-Gold) of human antibodies on human melanoma cells and subsequent expression of the obtained genes in mammalian cells [Orecchia P, Conte R, Balza E, Petretto A, Mauri P, Mingari M C, Carnemolla B. A novel human anti-syndecan-1 antibody inhibits vascular maturation and tumour growth in melanoma. Eur J Cancer. 2013 May; 49(8):2022-33. doi: 10.1016/j.ejca.2012.12.019. Epub 2013 Jan. 24]. It has been revealed that this antibody inhibits vessels maturation and tumor growth in the experimental human melanoma model (on mice). It has also been proven to be therapeutically effective in the human ovarian carcinoma model.

OC-46F2 represents a single-chain variable fragment (scFv)—a fusion protein consisting of variable fragments of a heavy ($V_H$) and a light ($V_L$-λ) immunoglobulin chains joined via a short linker peptide.

This compound does not contain constant antibody fragments, which complicates the adequate immune response associated with the use of antibodies formation, —the variable fragments of the molecule provide only junction with the antigen, determining the deterrent effect revealed by the authors. However, additional active compounds and, possibly, a production of conjugates are necessary for the tumor elimination in this case.

In such a way, the currently described murine antibodies to CD138 are not suitable for use in humans because of their high immunogenicity. They are used for laboratory purposes only. Chimeric MAbs do not possess any independent therapeutic effect—they are applied only as a targeting agent—and can also be immunogenic. An individual reaction of a patient to a particular MAb should not be ruled out. Besides, the active agent, targeted via antibody, or products of its degradation can become a stress factor for the human organism due to their structure, ability to decay, the decay period, and a character of compounds, to which it degrades. The exact structure of the natural human monoclonal antibodies to syndecan-1 is not established.

Taking into consideration the functional role of syndecan-1 in the invasive growth and metastatic propensity of the tumors, generation of more efficient and safe antibodies to it is a critical task at present.

This task is solved by the present invention which does not possess disadvantages of analogs.

The technical result of application of the present antibody specific to CD138 is at least in a spectrum spreading of MAbs, also to CD138, used in a tumor therapy, which allows providing treatment under idiocrasy or weak tolerance to analogs.

The technical result is in an increase of efficacy of the antibody to CD138. The revealed technical result is achieved by obtaining independent antitumor activity due to the use of the calculated and created by the authors proposed antibody of IgG4 isotype, represented by a particular combination of described sequences of antibody chains obtained by the inventors, as well as by the increased affinity to the antigen, also due to the use of the present antibody, also due to humanization of the antibody: due to the use of human antibody frameworks, it is possible to position the hypervariable regions more precise, which increases the correspondence of epitope and paratope, and therefore affinity.

The independent antitumor activity is achieved in one of embodiments of the invention by the fact that fragments of IgG3 chains mediating high antibody- and complement-dependent cytotoxicity are inserted into the constant fragment of the heavy chain of the IgG4 antibody, as a result such an antibody has an increased cytotoxic effect upon binding to CD138. Said technical result when using this embodiment of the invention is also achieved by the increase in antibody half-life period, which is achieved by introducing amino acid substitutions at the C-terminus of the constant part of the heavy chain. This allows achieving a longer effect, to use a lower dosage, perform fewer administrations of the antibody, which may also allow to reduce the cost of treatment.

The technical result of application of the present antibody to CD138 is also in an increase of safety of the anticancer drug. The indicated technical result is achieved by reducing immunogenicity due to the humanization of the antibody and also due to the fact that the active agent is a monoclonal antibody molecule—a protein, which degrades to amino acids afterwards, h.e. if applied, any consequences of non-clearance of an active agent (a nonprotein chemical compound) or products of its degradation within a certain time are excluded, as a result the decrease of stressing effect of the antitumor pharmaceutical on human organism is observed.

The technical result is also in an increase of efficacy, in simplification and fastening of the production, which allows lowering the price, which is achieved by obtaining higher expression rate of the antibody in mammalian cells at a short time due to codon optimization of the coding sequences, as well as to the insertion of signal secretion sequence at the N-terminus of the light and heavy chains.

DESCRIPTION OF THE INVENTION

The object of the present invention was creation of an efficient and safe universal anticancer drug, production of which is efficient, short-time and simple. This task is solved with the given monoclonal antibody specific to CD138 suitable for tumor therapy and possessing high affinity to the antigen (CD138), with individual anticancer activity and low immunogenicity, the active ingredient is the very molecule of the monoclonal antibody, protein by origin, which can be produced in high amounts in a short time in mammalian cells. In one embodiment, this problem is solved in that the proposed monoclonal antibody specific to syndecan-1 has a higher cytotoxicity and a long half-life period.

These properties of the obtained antibody are confirmed by research results given in the examples and are due to its structure expressed by use of the calculated and created by the inventors antibody chains, their particular combination and structure of the coding sequences.

A monoclonal antibody specific to syndecan-1, of IgG4 isotype is proposed, a heavy chain of which is characterized by the amino acid sequence SEQ ID NO:1, a light chain is characterized by the amino acid sequence SEQ ID NO:7, or a heavy chain is characterized by the amino acid sequence SEQ ID NO:5, a light chain is characterized by the amino acid sequence SEQ ID NO:3 or SEQ ID NO:7, the antibody is used as a self-acting substance for the therapy of tumor diseases. Also a monoclonal antibody specific to syndecan-1 of IgG4 isotype is proposed, in the constant fragment of a heavy chain of which IgG3 regions are contained, as well as amino acid substitutions at the C-terminus, to increase half-life, a heavy chain is characterized by the amino acid sequence SEQ ID NO:9, light chain-kappa and characterized by amino acid sequence SEQ ID NO:7, or a heavy chain is characterized by the amino acid sequence SEQ ID NO:11, a light chain-SEQ ID NO:3 or SEQ ID NO:7, the antibody is used as a self-acting substance for the therapy of tumor diseases. Also polynucleotides are provided encoding the chains of specific to syndecan-1 monoclonal antibody represented by the amino acid sequences SEQ ID NO:5 or SEQ ID NO:7 or SEQ ID NO:9 or SEQ ID NO:11, codon optimized for expression in producer cells. For expression in mammalian cells, each polynucleotide further comprises a fragment encoding a signal secretory sequence at the N-terminus cleaved upon secretion from the producer cells, codon optimized for expression in mammalian cells, and is characterized by SEQ ID NO:6 or SEQ ID NO:8 or SEQ ID NO:10 or SEQ ID NO:12.

BRIEF DESCRIPTION OF THE DRAWINGS

On FIG. 1,4,7 Kaplan-Meier survival curves are given.
On FIG. 2,5,8 the mean tumor growth by group, ±SEM, from the first day, is given.
On FIG. 3,6,9 group mean body weight change, BW, as a percentage, ±SEM, from the first day is given.
On all the figures: 1—control, 4—paclitaxel, on FIG. 1-3, for A549: 2—Mab4, 3—Mab6, on FIG. 4-6, for Colo 205: 2—Mab2, 3—Mab3, on FIG. 7-9, for PC3, 2—Mab 1, 3—Mab5.

EXAMPLES OF THE INVENTION REALIZATION

Figure 1:
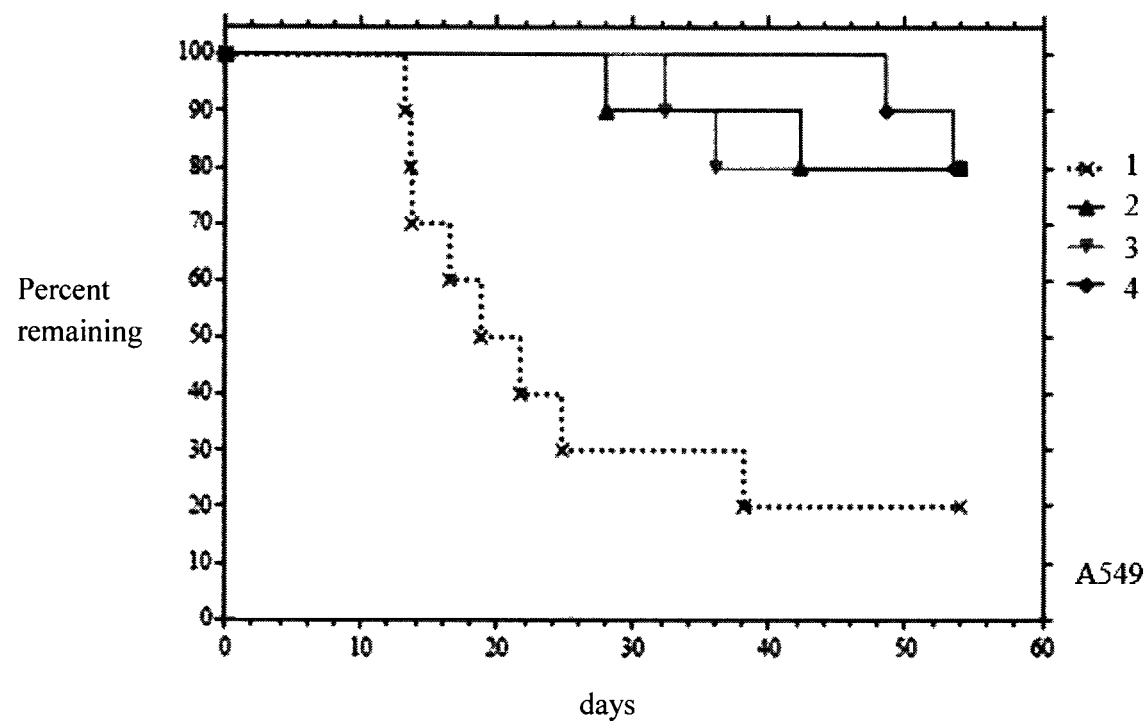

Example 1. Production of the Mab to Syndecan-1.

1.1. Production of Syndecan-1.

The gene encoding syndecan-1 was synthesized via chemical fermentative synthesis [Young L, Dong Q., Two step total gene synthesis method. Nucleic Acid Research: 32, e59, 2004] in two steps. The obtained gene was cloned in the vector pET151/D-TOPO, then the cells of *E. coli* BL21 (DE3)Star strain were transformed with it.

Fermentation of the producer strain and the recombinant protein extraction were performed. Syndecan-1 was purified via metal-chelate chromatography.

The recombinant protein had a purity of 98% and was used to obtain the hybridoma producing murine monoclonal antibodies to syndecan-1, and for testing of the obtained monoclonal antibodies.

1.2. Immunization of Balb/C Mice with Syndecan-1.

Immunization of Balb/C mice was performed. Purified recombinant syndecan-1 protein was used as an antigen. During the primary immunization, 50 µg of the antigen with the complete Freund's adjuvant (CFA) were injected subcutaneously into the mice. 28 days post inoculation, the level of immune response to the injected antigen was analyzed, estimating the titer of specific antibodies in serum via enzyme linked immunosorbent assay (ELISA). The animals with the highest level of immune response received 30 µg of the antigen with the incomplete Freund's adjuvant (IFA) subcutaneously once again, and the level of the secondary immune response was estimated 21 days post the injection. After that, 4-5 days before the somatic hybridization, 30 µg of the antigen in normal saline solution (NSS) were injected intraperitoneally.

1.3. Production of Hybridomas Synthesizing Monoclonal Antibodies Specific to Syndecan-1.

As the fusion partners, splenocytes of immunized mice with the serum antibody titer to the syndecan-1 protein of approximately 1:30000 and murine myeloma cells SP2/0-Ag14 (ATCC, CRL-1581) were used in the ratio of 2:1. The hybridization was performed with the help of polyethylene glycol solution (Sigma) according to the standard method. The stable hybrid cells selection was performed via cultivating in the IMDM medium (Iscove's Modified Dulbecco Medium, Sigma), containing 10% FCI serum (HyClone) and NAT (Gibco). The selection of the hybrid cell clones secreting the antibodies specific to the desired antigens was performed via enzyme linked immunosorbent assay (ELISA). As a result of primary screening, 10 hybrid cell clones producing monoclonal antibodies to syndecan-1 were selected. After the set of five clonings, 4 stable producer clones were obtained. Out of each cell line mRNA coding for heavy and light chains of the antibody to syndecan-1 was isolated.

1.4. Design of the Humanized Antibody to Syndecan-1

RNA was isolated from the stable clones of the hybrid cells, which produce monoclonal antibodies to syndecan-1, using "TRI Reagent" kit (Sigma, USA), according to the manufacturer's protocol. 1 ml of the lysing solution "TRI Reagent" was used per $(5-10) \cdot 10^6$ of the cells. The cDNA synthesis was performed with the Revert Aid® First Strand cDNA Synthesis Kit (Fermentas, Lithuania).

Amplification of genes coding for variable fragments of the murine antibodies was performed by PCR method using 5' degenerated primers for annealing on unknown $V_H$ and $V_L$ regions and the synthesized cDNA as a matrix. Amplification of the DNA fragments to be cloned was performed by PCR with a highly accurate thermostable DNA-polymerase Pfx. The obtained PCR-products were cloned into the pGMT-easy vector using Fast Ligation Kit, Fermentas, and sequenced according to the Sanger method. It was found that hybridoma 1 and hybridoma 2 synthesize different MAbs, which were used to obtain the monoclonal antibody of the invention.

The results of the sequencing were used to obtain the humanized monoclonal antibody.

The antibody humanization was performed by the transfer of the detected (estimated with the help of computer algorithms on the obtained nucleotide sequences) hypervariable regions (CDRs) of the variable fragments of the murine antibodies responsible for complementarity to the antigen, onto the human variable fragment; the CDRs were positioned between the appropriate framework regions, according to the results of the data banks analysis and bioinformatic modeling of structural analogy between the antibodies. The obtained humanized antibodies possess specificity of the maternal murine antibody, but also have a higher affinity, in consequence of a more suitable three-dimensional position of CDRs, due to the framework regions.

The following programs were used for molecular graphics: Insight II; Accelrys, CA. Modeling of the conformational homology between the murine donor antibody and human acceptor antibody was performed via WAM (http://antibody.bath.ac.uk), SWISS-MODEL (http://www.expasy.org), INSIGHT-HOMOLOGY (Accelrys), COMPOSER (Tripos, MO), and GCG Wisconsin Package. The sequences of the murine antibody variable fragments were annotated and indexed via Kabat and Chothia data bases.

Information about the structure of the variable fragments is taken into consideration by the indexing developed by Chothia [Chothia C, Lesk A M. Canonical structures for the hypervariable regions of immunoglobulins. J Mol Biol. 1987 Aug. 20; 196(4): 901-17]. However, the amino acid residues in the variable fragments of antibodies are not considered by this indexing. Concerning the data for indexing and annotation of variable fragments mentioned above, Kabat and Chothia modified algorithm—Abhinandan K R and Martin A C—were applied [Abhinandan K R and Martin A C. Analysis and Prediction of VH/VL Packing in Antibodies, Protein Engineering Design and Selection. 2010, Abhinandan K R, Martin A C. Analysis and improvements to Kabat and structurally correct numbering of antibody variable domains. Mol Immunol. 2008 August; 45(14): 3832-9]. During the indexation, not only the corrected data from multiple antibody sequences alignment by Kabat and structural CDR data by Chothia considering the FR structure were taken into account, but also the $V_H/V_L$ angles folding in the donor and acceptor antibodies. For the automatic annotation, programs with interactive web-interface were used: SeqTest (AbCheck) http://www.bioinf.org.uk/abs/seqtest.html, Abnum http://www.bioinf.org.uk/abs/abnum/, the manual correction and validation were performed via a local version of the Kabat data base http://www.kabatdatabase.com/index.html and the program KabatMan http://www.bioinf.org.uk/abs/simkab.html, as well as IMGT http://imgt.cines.fr/, as well as with the help of corrected data from multiple variable fragment fitting of the antibody sequences via MUSCULE http://www.ebi.ac.uk/Tools/muscle/index.html, and the program package FASTA http://fasta.bioch.virginia.edu/fasta_www2/fasta_down.shtml, the structures of which had been presented in PDB for 2012, as well as by several Perl scripts for automatic data analysis, developed by the authors of the present invention. $V_H/V_L$ angles were calculated and predicted based on the algorithm offered by Abhinandan [Abhinandan K. R., 2010]. All necessary calculations related to the molecular structure modeling of proteins were performed using Modeller and Swiss-Model.

The next step for humanizing of the antibodies was a choice of the acceptor variable fragments of the human antibodies for transfer. The right choice of the human acceptor antibody ensures to almost 100% a successful humanization of the antibody with the Kd-value being enough for a high strength binding with the antigen. By the methods of molecular modeling and the approaches mentioned above, structural models of the variable fragments of the revealed murine monoclonal antibodies to syndecan-1 were constructed. Using the obtained 3D models, the most homological (especially considering the key positions) sequences of the human acceptor antigens were estimated, whereas only antibody with the "humanity" coefficient of H>1 were applied (which can potentially decrease the HAHA response). Based on the obtained models, amino acid sequences of the variable fragments of heavy and light (κ) chains of the antibodies were estimated.

1.5. Production of Monoclonal Antibodies to Syndecan-1

Amino acid sequences of the constant and the calculated variable fragment of the heavy chain were joined to one amino acid sequence (SEQ ID NO:5 -respectively to hybridoma 1). Sequences of the constant and the calculated variable kappa light chain fragments were joined into a single amino acid sequence (SEQ ID NO:7 -respectively to hybridoma 2).

Additionally, a chimeric heavy chain for the obtained hybridoma 2 and a light chain—for the hybridoma 1 were constructed. Amino acid sequences of the murine variable and human constant fragments of the heavy chain were connected (SEQ ID NO:1, respectively to hybridoma 2). Amino acid sequences of the murine variable and human constant fragments of Kappa light chain were also connected (SEQ ID NO:3—respectively to hybridoma 1).

Obtained amino acid sequences were transferred into nucleic acid ones, further a fragment was added to the N-terminus encoding the signal secretory sequence cleaved upon secretion from the producer cells, and codon optimization was conducted for the increased production of these antibodies in mammalian cells (CHO) using a program on site http://www.encorbio.com/protocols/Codon.htm.

As a result, a final version of the nucleotide sequences was obtained (SEQ ID NO: 2, SEQ ID NO: 4, SEQ ID NO: 6, SEQ ID NO: 8) encoding the chains of monoclonal antibodies to syndecan-1 (SEQ ID NO: 1, SEQ ID NO: 3, SEQ ID NO: 5, SEQ ID NO: 7), which were then synthesized using chemical synthesis.

Also antibodies were obtained modified to perform increased activity. For this IgG3 fragments with the highest complement system activation rate out of all isotypes, as well as the highest Fc receptor binding affinity to phagocytes were inserted in the IgG4 heavy chain constant fragment. Amino acid substitutions were also inserted in the C-terminal region of the IgG4 constant fragment for the purpose of the increase of the antibody half-life.

The sequences of the estimated heavy chain variable and constant fragments were connected to one sequence (SEQ ID NO: 9—respectively to hybridoma 1).

Such variant of a heavy chain was also received on the basis of a chimeric heavy chain, created based on a murine one obtained from the hybridoma 2, as a result of connection of amino acid sequences of murine variable and the calculated human constant fragment of the heavy chain into one amino acid sequence (SEQ ID NO:11).

Nucleotide sequences were calculated on the basis of the amino acid sequences of the protein, additionally a fragment on the N-terminus was introduced coding for the secretory sequence released while secretion from the producer cells and codon optimization was also performed for the purpose of increase of the present antibodies production in mammalian cells (CHO), with the help of the program from the internet-site http://www. encorbio.com/protocols/Codon.htm.

As a result, the final version of the nucleotide sequences (SEQ ID NO:10, SEQ ID NO:12) coding for the heavy chains of monoclonal antibodies to syndecan-1 with IgG4-IgG3 shift (SEQ ID NO:9, SEQ ID NO:11) was obtained. The obtained nucleotide sequences were synthesized chemically. The synthesized fragments were cloned in the plasmid vector pUC57 for amplification and then recloned in the vector pcDNA3.1+ for the purpose of transfection of mammalian cells.

Then producer cells of monoclonal antibodies to syndecan-1 were created. The present inventors have made an original decision to create producers of antibodies, not only derived from hybridomas 1 and 2, but also created by a combination of the calculated heavy and light chains.

A transfection of competent mammalian cells (CHO) was performed by two created plasmid DNA, each carrying, respectively, a polynucleotide codon-optimized for expression in mammalian cells encoding a heavy or light chain of an antibody, with secretory sequence.

Mammalian cells transfection with the produced plasmids was performed by calcium-phosphate-precipitation method.

Mammalian cells (CHO) were seeded into 12-well plates (Costar, USA) at a density of $5 \cdot 10^4$ cells/sm². The next day, culture medium was changed for the purpose of synchronization of cell divisions. Three hours later, calcium-phosphate precipitated plasmid DNA was added to the cells. To prepare the precipitate, 250 µl of the solution containing 50 µg of the DNA in 250 mM $CaCl_2$ were mixed slowly with 250 µl of the solution (1.64% NaCl, 1.13% HEPES pH 7.12 and 0.04% $Na_2HPO_4$). After 24 hours of incubation at 37° C., 5% $CO_2$, medium was changed to the analogous one, containing additionally 2 antibiotics: 80 µg/ml zeocin and 2 µg/ml blasticidin S for the selection of clones, containing both transformed plasmids and, consequently, synthesizing the full-length monoclonal antibodies. The selection was being performed for 20 days in wells containing alive cells; the medium was changed (with the previous culture medium being not discarded, but used for measuring of the antibody secretion via ELISA). A day later the cells were detached from the well-bottom, and the expression of the transformed genes was analyzed. The analysis of the transfection efficacy was performed on a flow cytometer EPICS XL Beckman Coulter (Beckman Coulter, USA).

The level of monoclonal antibodies in a culture medium of obtained stable transfectomas of the CHO cell line was analyzed with the help of standard solid-phase ELISA.

As a result of 7 clonings stable CHO transfectomas were obtained and accumulated for cryoconservation and pilot-scale production of antibodies. The productivity of the obtained CHO transfectomas synthesizing antibodies to syndecan-1 based on SEQ ID NO:1 and SEQ ID NO:7 (hereinafter—Mab2), and SEQ ID NO:5 and SEQ ID NO:3 (hereinafter—Mab1) was about 550 µg/$10^7$ cells/a day. The productivity of the created CHO transfectomas synthesizing antibodies to syndecan-1 on the basis of SEQ ID NO:1 and SEQ ID NO:3 (hereinafter—Mab3), and SEQ ID NO:5 and SEQ ID NO:7 (hereinafter—Mab4) was about 650 µg/$10^7$ cells/a day, based on SEQ ID NO:11 and SEQ ID NO:3 (hereinafter—Mab7), and SEQ ID NO:11 and SEQ ID NO:7 (hereinafter—Mab6)—about 650 µg/$10^7$ cells/a day. Productivity of the created CHO transfectomas synthesizing antibodies to syndecan-1 on the basis of SEQ ID NO:9 and SEQ ID NO:7 (hereinafter—Mab5) was about 700 µg/$10^7$ cells per day.

Monoclonal antibodies of the invention may be obtained using other mammalian cells, e.g., HEK293, COS.

1.6. Culturing of Cells Producing Monoclonal Antibodies to Syndecan-1

Cultivation of producer cells was performed using a bioreactor BIOSTAT® Bplus and autoclaved IMDM medium supplemented with 45 g DFBS (0.5%) and 25.8 g (100 mmol) of zinc sulfate heptahydrate ($ZnSO_4 \times 7H_2O$) per 9 liters of medium. The operating mode was set: temperature 37° C., pH 6.9-7.2, the concentration of oxygen 50% of air saturation. After reaching of the preset mode the seeding of the bioreactor was performed, for which in aseptic conditions a seed material was introduced. The culturing was performed for 3 days.

Upon completion of the cultivation, the culture liquid was filtered through a sterile capsule «Sartopure» («Sartorius», Germany) with a pore diameter of 1.2 micrometers, at a rate of 1 L/min. The clarified liquid was concentrated using Viva Flow System 200 («Sartorius», Germany) using a 50 kDa filter. Concentration was performed until obtaining a total volume of 200 mL.

1.7. Purification of the Obtained Monoclonal Antibodies to Syndecan-1

Chromatographic purification was carried out in two stages, using sterile solutions. On the first stage BioLogic DuoFlow Pathfinder (Bio-Rad) system was used with an automatic fraction collector BioFract and a semipreparative chromatography column YMC TriArt, 250×4.6 mm, C18 sorbent. Before starting work the column was equilibrated with 200 ml of buffer (1 kg of water for injections and 1 g of trifluoroacetic acid) in a manual mode through the chromatograph pump at a rate of 2 ml/min.

A prepared material in a volume of 200 ml was put through the pump into the chromatograph at a speed of 0.5 mL/min. Elution was performed with buffer (2 kg of acetonitrile, 2 g of trifluoroacetic acid) at a rate of 0.5 mL per minute. The fraction was collected at the maximum absorbance at 260 nm. The volume of the fraction was about 500 mL.

The fraction was collected at the maximum of absorbance at 260 nm. The volume of fraction was about 500 mL.

A second purification step was performed using gel chromatography column BioSil SEC 125-5, 300×7,8 mm. The column was preliminarily equilibrated with 0.02 M PBS-buffer. The obtained material was introduced into the chromatograph through the chromatograph pump at a rate of 0.5 ml/min. Elution was performed with buffer (0.6 M NaCl solution) with a concentration gradient from 0.1 to 0.6 M. The fraction having an absorbance at A280 nm no less than 3.4 absorbance units was collected. The fraction was collected in vials. The volume of the resulting solution was approximately 1 liter with the concentration of antibody 2-4 mg per 1 ml.

Kd of the obtained antibodies was measured by ELISA, using Scatchard equation.

For antibody characterized by amino acid sequences SEQ ID NO:5 and SEQ ID NO:3 (Mab1), Kd=$8.5*10^{-9}$. For antibody characterized by amino acid sequences SEQ ID NO:1 and SEQ ID NO:7 (Mab2), Kd=$7.8*10^{-9}$. For antibody characterized by amino acid sequences SEQ ID NO:1 and SEQ ID NO:3 (Mab3), Kd=$7,0*10^{-9}$, SEQ ID NO:5 and SEQ ID NO:7 (Mab4)—$6,7*10^{-99}$. For antibody characterized by amino acid sequences SEQ ID NO:11 and SEQ ID NO:3 (Mab7), Kd=$6,0*10^{-9}$, SEQ ID NO:11 and SEQ ID NO:7 (Mab6)—$6,9*10^{-9}$. For antibody characterized by amino acid sequences of SEQ ID NO:9 and SEQ ID NO:7 (Mab5), Kd=$5.0*10^{-9}$.

Thus, the created antibodies possess affinity sufficient for effective antigen binding.

Example 2. The Study of Antitumor Effect of the Monoclonal Antibodies to Syndecan-1.

The study of antitumor activity of the generated antibodies was held using xenograft models of human tumors in BALB/c NUDE mice. In each tumor model two-three types of the monoclonal antibodies to syndecan-1 were studied.

Mice

For research female athymic BALB/c NUDE mice were used. The animals were fed NIH 31 Modified and Irradiated Lab Diet® and water ad libitum. The mice were housed on a 12-hour light cycle at 20-22° C. and 40-60% humidity.

The tumor volume was calculated using the formula: w2*½, where w=width and 132 length, of tumor, in mm. Tumor weight was estimated with the assumption that 1 mg is equivalent to 1 mm$^3$ of tumor volume.

Therapeutic Agent and a Method of its Administration

The antibodies under study were held in a 2.5 mg/mL stock solution and were stored at 4° C. protected from light. The dosing solution delivered dosage of 0.5 mg/animal in a fixed volume of 0.2 mL/animal. Dosing solution was stored at 4° C. protected from light.

Paclitaxel (Lot CP2N10007) was purchased as a dry powder (Fort Worth, Tex.). A paclitaxel stock solution (30 mg/mL) in 50% ethanol: 50% Cremophor EL was prepared and stored at room temperature protected from light. On each day of dosing, an aliquot of the paclitaxel stock was diluted with 5% dextrose in water (D5W) to yield a 3.0 mg/mL paclitaxel dosing solution in a vehicle consisting of 5% ethanol: 5% Cremophor EL: 90% D5W. The dosing solution delivered a dosage of 30 mg/kg in a dosing volume of 10 mL/kg.

PBS ("Vehicle") was used to dose the vehicle control group.

Vehicle and antibodies were dosed intraperitoneally twice weekly for four weeks. Paclitaxel was delivered intravenously once every other day for a total of five doses. Group 1 received vehicle and served as the benchmark group for tumor engraftment and progression, as well as the control for tumor growth delay analysis (TGD).

Evaluation of the Study Results

Each animal was euthanized when its tumor reached the volume endpoint. The time to endpoint (TTE) for each mouse was calculated with the following equation: ($\log_{10}$ (endpoint volume)—b)/m, where b is the intercept, m is the slope of the line obtained by linear regression of log-transformed tumor growth data set. The data set is comprised of the first observation that exceeded the study endpoint volume and the three consecutive observations that immediately preceded the attainment of the endpoint volume. Any animal that did not reach endpoint was euthanized at the end of the study and assigned a TTE value equal to the last day of the study. In instances in which the log-transformed calculated TTE preceded the day prior to reaching endpoint or exceeded the day of reaching tumor volume endpoint, a linear interpolation was performed to approximate the TTE. Any animal determined to have died from treatment-related (TR) causes was assigned a TTE value equal to the day of death. Any animal that died from non-treatment-related (NTR) causes was excluded from the analysis.

Treatment outcome was evaluated from tumor growth delay (TGD), which was defined as the increase in the median TTE for a treatment group compared to the control group, TGD=T−C, expressed in days, or as a percentage of the median TTE of the control group, %TGD=(T−C)*100/C, where T—median TTE for a treatment group, C—median TTE for the control group.

Toxicity

The mice were observed frequently for health and overt signs of any adverse TR side effects. Individual BW loss was monitored per protocol, and any animal whose weight exceeded the limits for acceptable BW loss was euthanized. If group mean BW recovered, dosing was resumed in that group, but at a lower dose or less frequent dosing schedule. Acceptable toxicity was defined as a group mean BW loss of less than 20% during the study and not more than one TR death among ten treated animals, or 10%. Any dosing regimen resulting in greater toxicity was considered the maximum tolerated dose (MTD). A death was classified as TR if it was attributable to treatment side effects as evidenced by clinical signs and/or necropsy, or could also be classified as TR if due to unknown causes during the dosing period or within 14 days of the last dose. A death was classified as NTR if there was evidence that the death was related to the tumor model, rather than treatment-related.

Statistical and Graphical Analysis

Prism 6.05 (GraphPad) for Windows was employed for statistical and graphical analyses. Survival was analyzed by the Kaplan-Meier method, based on TTE values. The logrank (Mantel-Cox) and Gehan-Breslow-Wilcoxon tests determined the significance of the difference between the overall survival experiences (survival curves) of two groups, based on TTE values. The Kaplan-Meier plot and statistical tests share the same data sets, and exclude any animals that were recorded as NTR deaths. The two-tailed statistical analyses were not adjusted for multiple comparisons, and were conducted at P=0.05.

Because statistical tests are tests of significance and do not provide an estimate of the size of the difference between groups, all levels of significance are described as either significant or non-significant.

Tumor growth curves were truncated after two TR deaths occurred in the same group. Group mean BW changes over the course of the study were graphed as percent change, ±SEM, from day 1. Tumor growth and BW change curves were truncated after more than half the assessable mice in a group exited the study.

2.1. Study of the Efficacy of Humanized Monoclonal Antibodies to Syndecan-1 (Mab4, Mab6) using the A549 Cell Line The mice were eleven weeks old on day 1 of the study and had a BW range of 18.4 to 25.6 g.

Xenografts were initiated with A549 human non-small cell lung carcinoma cells cultured in Kaighn's modified Ham's F12 medium containing 10% fetal bovine serum, 100 units/mL penicillin G, 100 µg/mL streptomycin sulfate, 2 mM glutamine, 1 mM sodium pyruvate, and 25 µg/mL gentamicin. Cells were cultured in tissue culture flasks in a humidified incubator at 37° C., in an atmosphere of 5% $CO_2$ and 95% air.

The A549 tumor cells used for implantation were harvested during log phase growth and resuspended in 50% Matrigel matrix (BD Biosciences) in phosphate buffered saline (PBS) at a concentration of $5 \times 10^7$ cells/mL. Each test mouse was injected subcutaneously in the right flank with $1 \times 10^7$ A549 cells (0.2 mL cell suspension), and tumor growth was monitored as the average size approached the target range of 150 to 220 mm$^3$. Tumors were measured in two dimensions using calipers, and volume was calculated.

Twenty-four days after tumor cell implantation, on day 1 of the study, animals were sorted into 4 groups (n=10/group) with individual tumor volumes of 126 to 221 mm$^3$, and group mean tumor volumes of 185-186 mm$^3$. Tumors were measured with a caliper twice weekly for the first 45 days of the study and additionally on Day 54.

The study endpoint was a tumor volume of 800 mm³ or Day 54, whichever came first.

Figure 2:
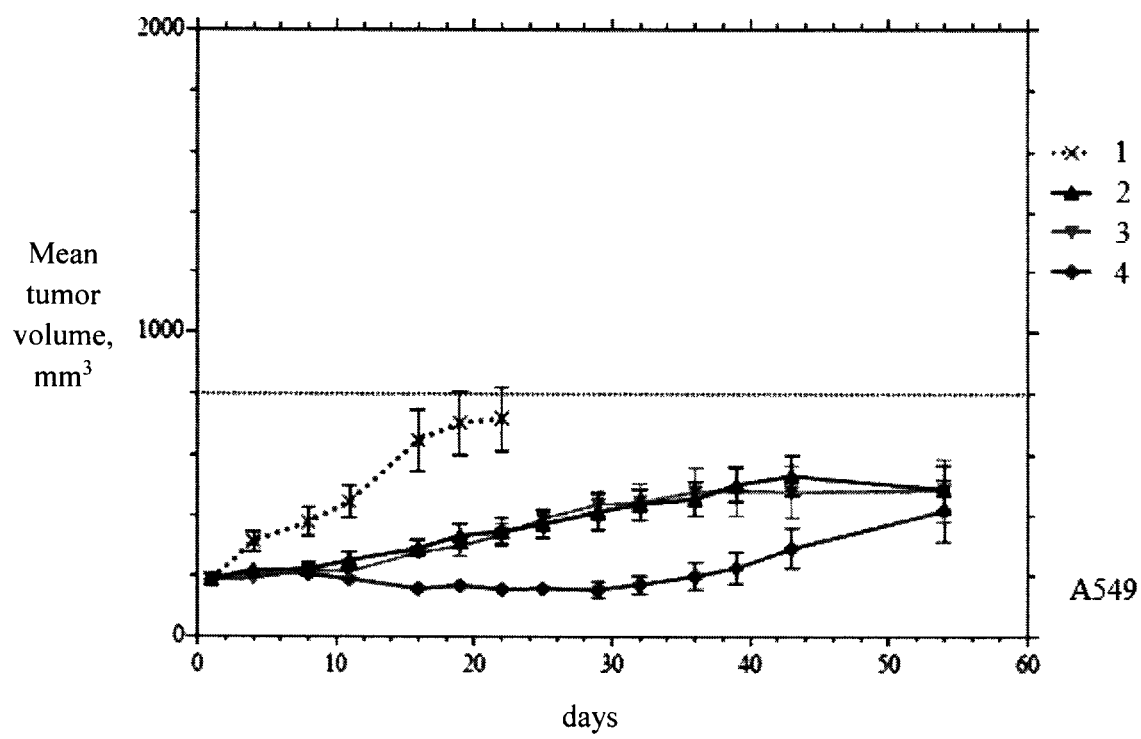
Figure 3:
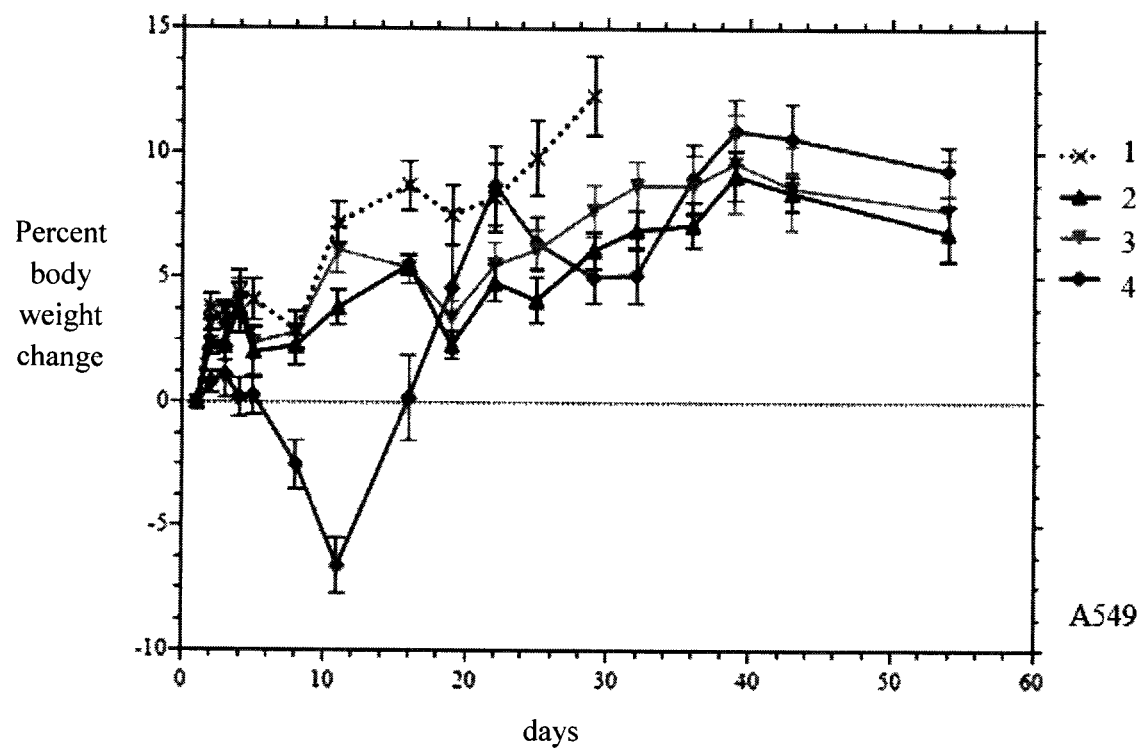

The results of the study are shown on FIG. 1-3.

2.2. Study of the Efficacy of the Monoclonal Antibodies to Syndecan-1 (Mab2, Mab3) Using Colo205 Cell Line Mice were nine weeks old on day 1 of the study and had a BW range of 17.8 to 23.8 g.

Xenografts were initiated with human colorectal adenocarcinoma cells (Colo 205) cultured in RPMI 1640 medium containing 10% fetal bovine serum, 2 mM glutamine, 1 mM sodium pyruvate, 10 mM HEPES, 0.075% sodium bicarbonate, 100 units/mL penicillin G, 100 µg/mL streptomycin sulfate and 25 µg/mL gentamicin. Cells were cultured in tissue culture flasks in a humidified incubator at 37° C., in an atmosphere of 5% $CO_2$ and 95% air.

The Colo 205 tumor cells used for implantation were harvested during log phase growth and resuspended in 50% Matrigel matrix (BD Biosciences) in phosphate buffered saline (PBS) at a concentration of $5 \times 10^6$ cells/mL. Each test mouse was injected subcutaneously in the right flank with $1 \times 10^6$ Colo 205 cells (0.2 mL cell suspension), and tumor growth was monitored as the average size approached the target range of 100 to 150 mm³. Tumors were measured in two dimensions using calipers, and volume was calculated.

In ten days post tumor cells implantation, on day 1 of the study, animals were sorted into four groups (n=10) with individual tumor volumes of 88 to 162 mm³, and group mean tumor volumes of 123-127 mm³. Tumors were measured with a caliper twice weekly for the first 60 days of the study and additionally on days 65 and 75.

The study endpoint was a tumor volume of 1500 mm³ or day 75, whichever came first.

Figure 4:
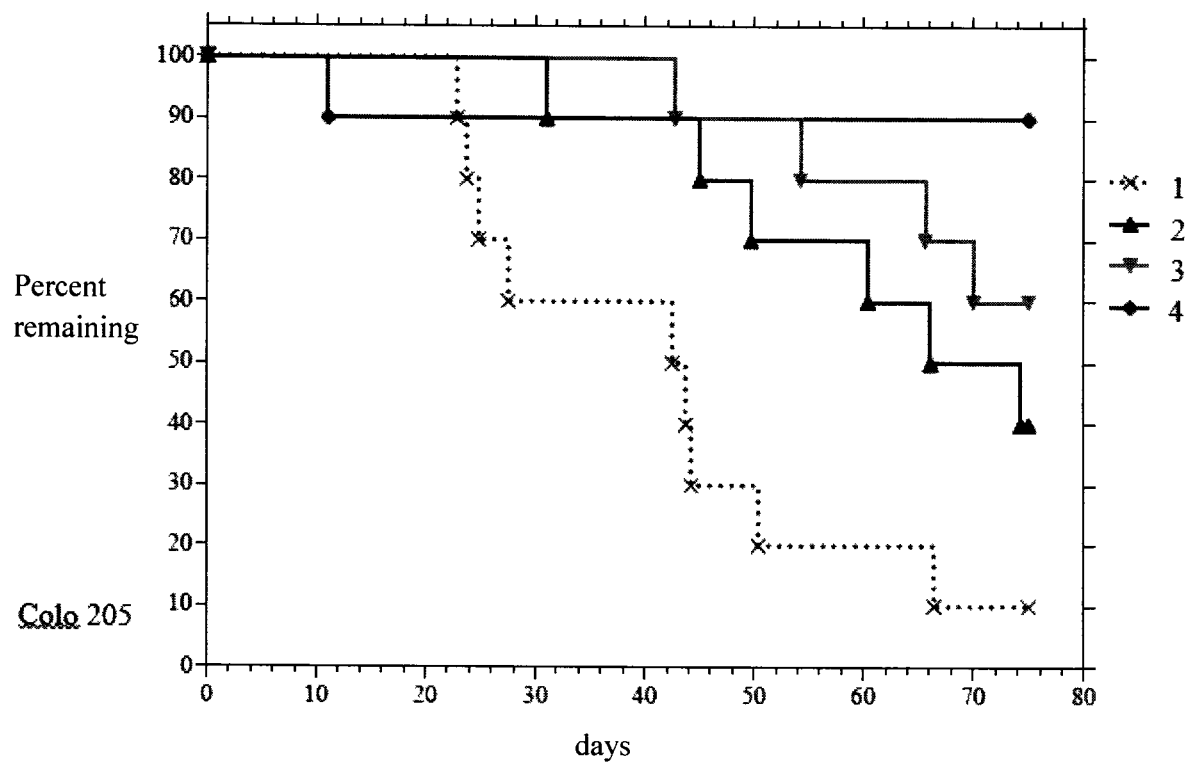
Figure 5:
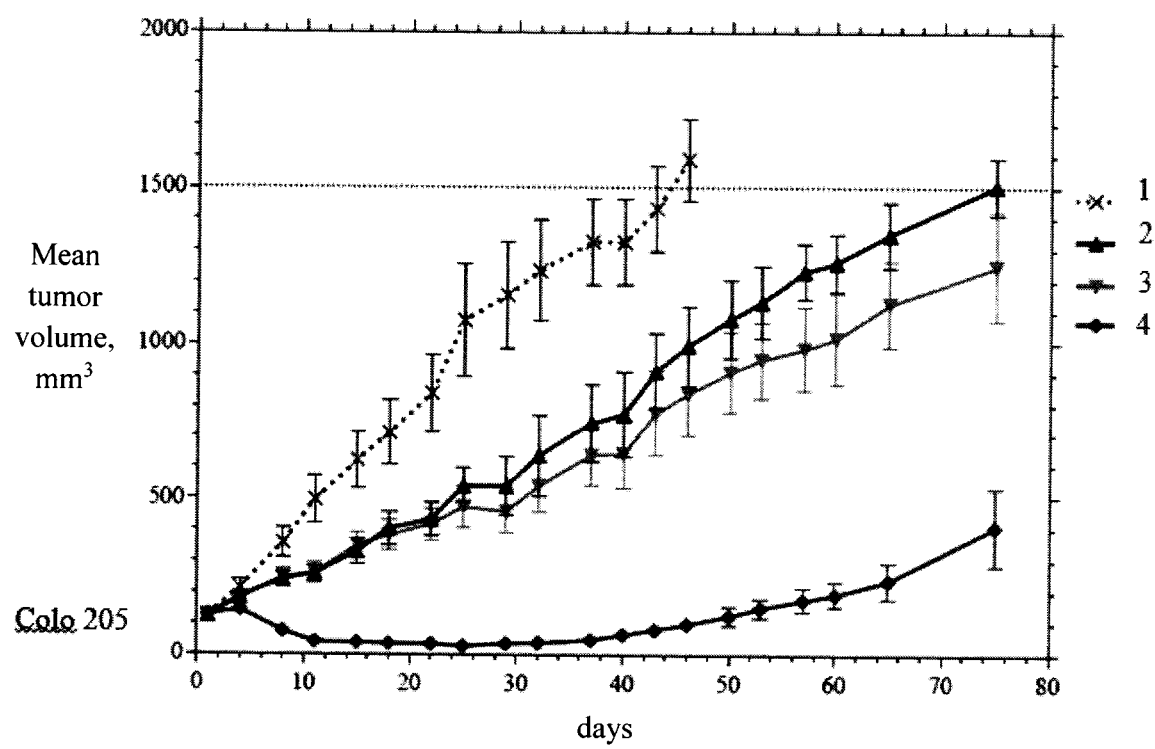
Figure 6:
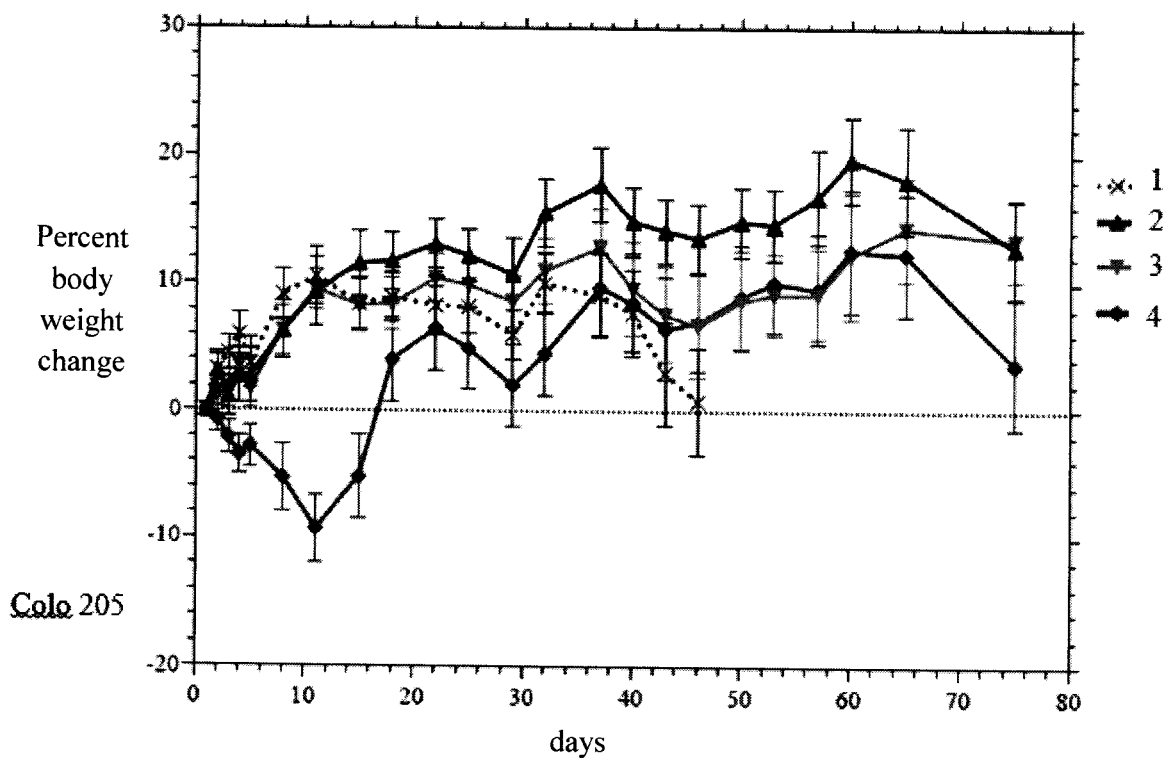

The results of the study are shown on FIG. 4-6.

In paclitaxel group a TR death was revealed on the day 11 of the study.

2.3. Study of the Efficacy of Humanized Monoclonal Antibodies to Syndecan-1 (Mab 1, Mab5) Using the PC3 Cell Line Mice were 11 weeks old on day 1 of the sudy and had a BW range of 19.1 to 26.4 g.

Xenografts were initiated with androgen-independent PC3 tumor line cells, derived from a human prostatic cancer metastatic to bone, and displayed the morphology of a poorly-differentiated adenocarcinoma. The tumors utilized for the present study were maintained by serial engraftment in female nude mice. To initiate tumor growth, a 1 mm³ fragment was implanted subcutaneously in the right flank of each test animal. The tumors were calipered in two dimensions to monitor growth as their mean volume approached the desired 100-150 mm³ range.

Twenty six days after tumor fragment implantation, on day 1 of the study, mice were sorted into four groups (n=10/group) with individual tumor volumes of 63-196 mm³, and group mean tumor volumes of 119-120 mm³. Tumors were measured with a caliper twice weekly for the first 45 days of the study and additionally on day 53.

The study endpoint was a tumor volume of 1500 mm³ or day 53, whichever came first.

Figure 7:
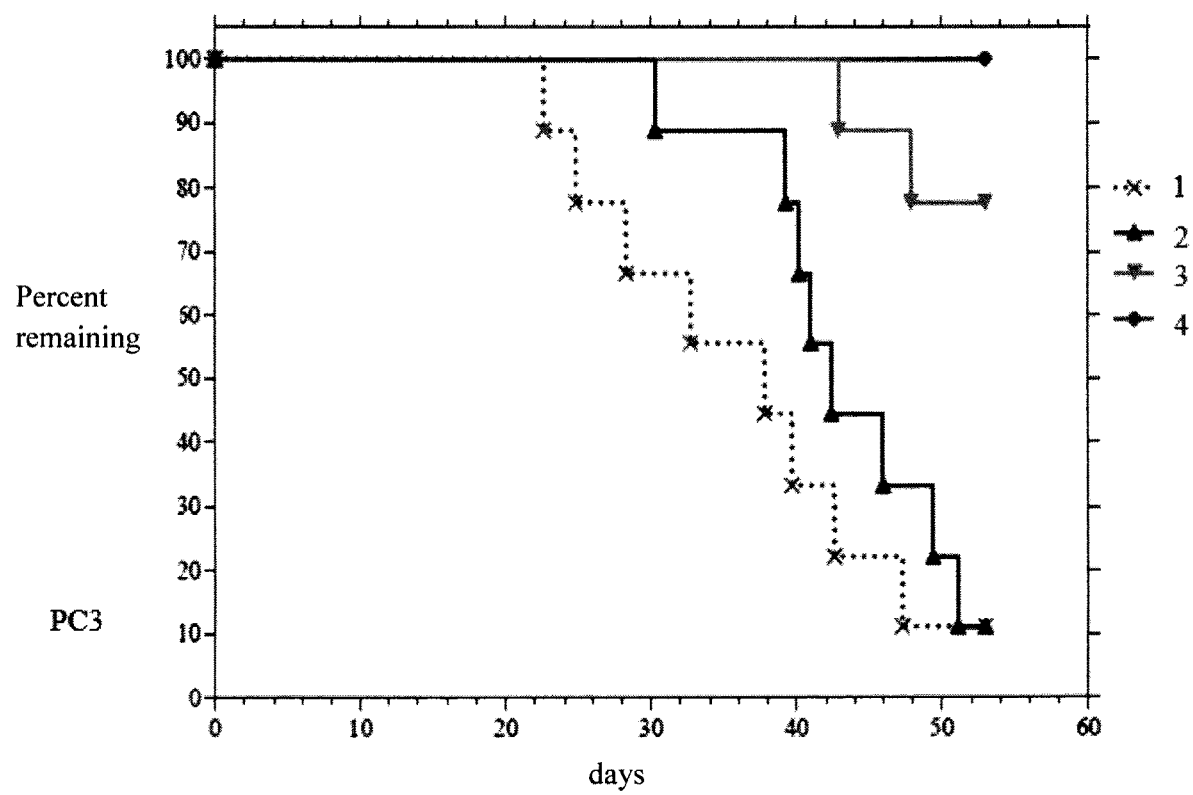
Figure 8:
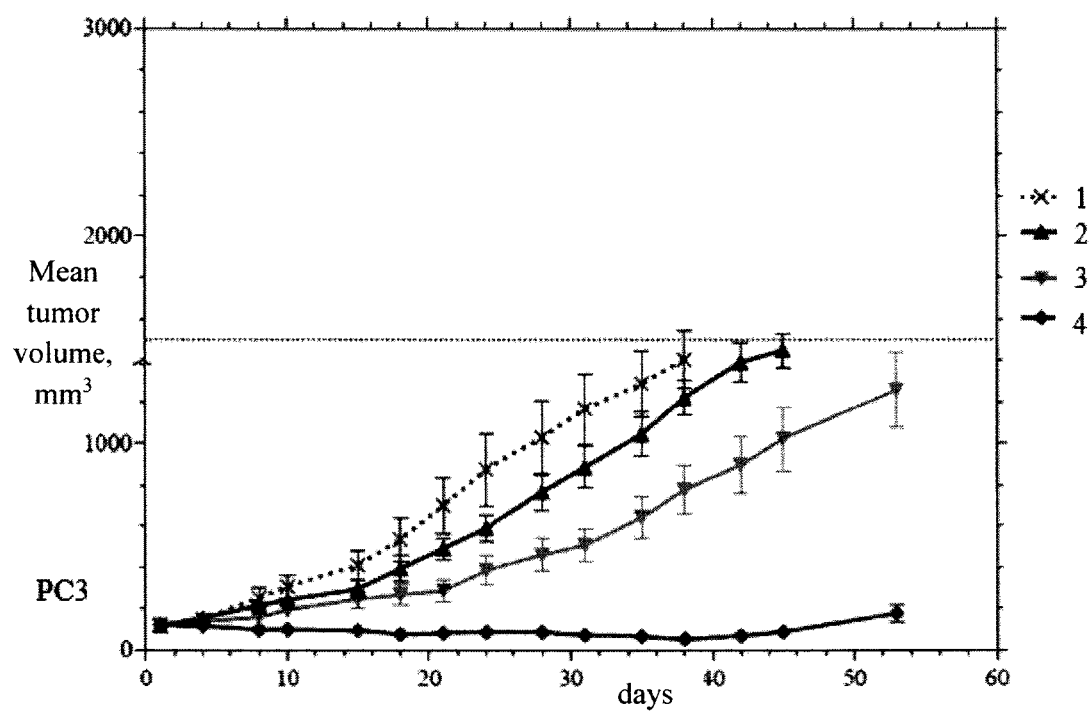
Figure 9:
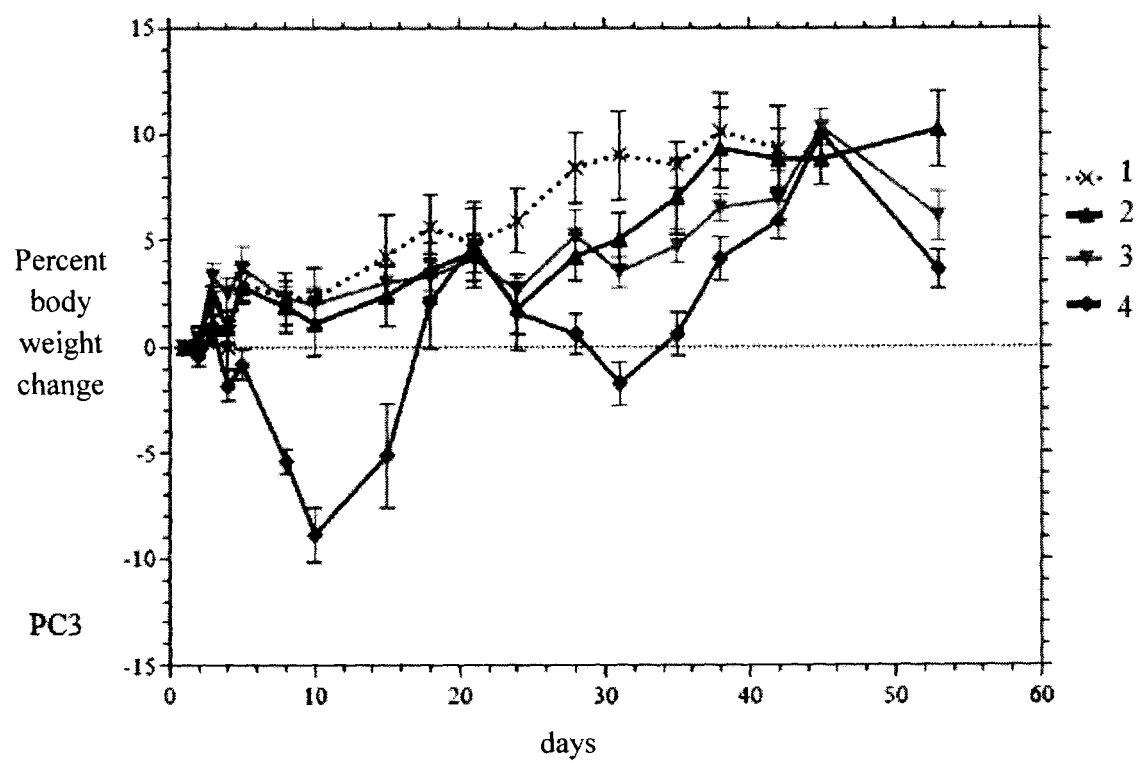

The results of the study are shown on FIG. 7-9.

Analyzed antibodies (Mab4 and Mab6, Mab2 and Mab3, Mab1 and Mab5) have demonstrated statistically significant efficacy, as compared with the control group, on all the investigated parameters, comparable to that of paclitaxel, and also a lack of side effects, which means also the safety of these agents. Mab7 analysis has revealed similar rates to those of Mab6.

The invention claimed is:

1. A monoclonal antibody specific to syndecan-1, comprising a heavy chain set forth as SEQ ID NO:1 or SEQ ID NO:9, and a light chain set forth as SEQ ID NO:7.

2. A monoclonal antibody specific to syndecan-1, comprising a heavy chain set forth as SEQ ID NO:5 or SEQ ID NO:11, and a light chain set forth as SEQ ID NO:3 or SEQ ID NO:7.

3. A polynucleotide encoding a chain of a monoclonal antibody specific to syndecan-1, characterized in that the polynucleotide is codon-optimized for expression in producer cells, wherein the chain is set forth as SEQ ID NO:5, or SEQ ID NO:7, or SEQ ID NO:9, or SEQ ID NO:11.

4. The polynucleotide of claim 3, wherein the polynucleotide is codon optimized for expression in mammalian cells.

5. A polynucleotide according to claim 3, characterized in that the polynucleotide contains a fragment coding for a secretory signal sequence at the N-terminus cleaved upon secretion from the producer cells, and wherein the polynucleotide is codon optimized for expression in mammalian cells, set forth as SEQ ID NO:6 or SEQ ID NO:8 or SEQ ID NO:10 or SEQ ID NO:12.

6. A method of treating tumor diseases comprising administering the monoclonal antibody of claim 1.

7. The method of claim 6, wherein the antibody is used as a self-acting substance.

8. A method of treating tumor diseases comprising administering the monoclonal antibody of claim 2.

9. The method of claim 8, wherein the antibody is used as a self-acting substance.

* * * * *